United States Patent [19]

Bryant

[11] 4,191,749

[45] Mar. 4, 1980

[54] METHOD AND MATERIAL FOR INCREASING THE PERCENTAGE OF MAMMALIAN OFFSPRING OF EITHER SEX

[76] Inventor: Bernard J. Bryant, 509 Scripps Dr., Davis, Calif. 95616

[21] Appl. No.: 841,207

[22] Filed: Oct. 11, 1977

[51] Int. Cl.$^2$ .................. A61K 35/52; C12K 9/00; A61K 39/00

[52] U.S. Cl. .................................. 424/105; 435/2; 424/85; 424/88

[58] Field of Search ................ 424/85, 88, 12, 105; 195/1.8

[56] References Cited

U.S. PATENT DOCUMENTS

| | | | |
|---|---|---|---|
| 3,687,806 | 8/1972 | Bovenkamp | 424/85 |
| 3,692,897 | 9/1972 | Bhattacharya | 424/85 |
| 4,021,364 | 5/1977 | Speiser et al. | 424/85 |
| 4,092,116 | 5/1978 | Giaever | 424/12 |

*Primary Examiner*—Sam Rosen
*Attorney, Agent, or Firm*—Mark C. Jacobs

[57] ABSTRACT

Method, apparatus and material are disclosed for increasing the percentage of mammalian offspring of either sex. The method utilizes a male-specific antibody coupled to a solid-phase immunoabsorbent material to effect a separation of sex-determining spermatazoa derived from a semen suspension. The male-specific antibody selectively binds male-determining spermatazoa. The female-determining spermatazoa are not bound and are recovered directly from the male-specific antibody-coated immunoabsorbent material. The male-determining spermatazoa are recovered from the male-specific antibody-coated immunoabsorbent material after altering the condition thereof to inhibit binding. The apparatus includes a vertical surface comprising beads of immunoabsorbent material over which are distributed male-specific antibodies. The materials are two seminal fluids, one having a substantial preponderance of male-determining spermatazoa, and the other having a substantial preponderance of female-determining spermatazoa.

14 Claims, 1 Drawing Figure

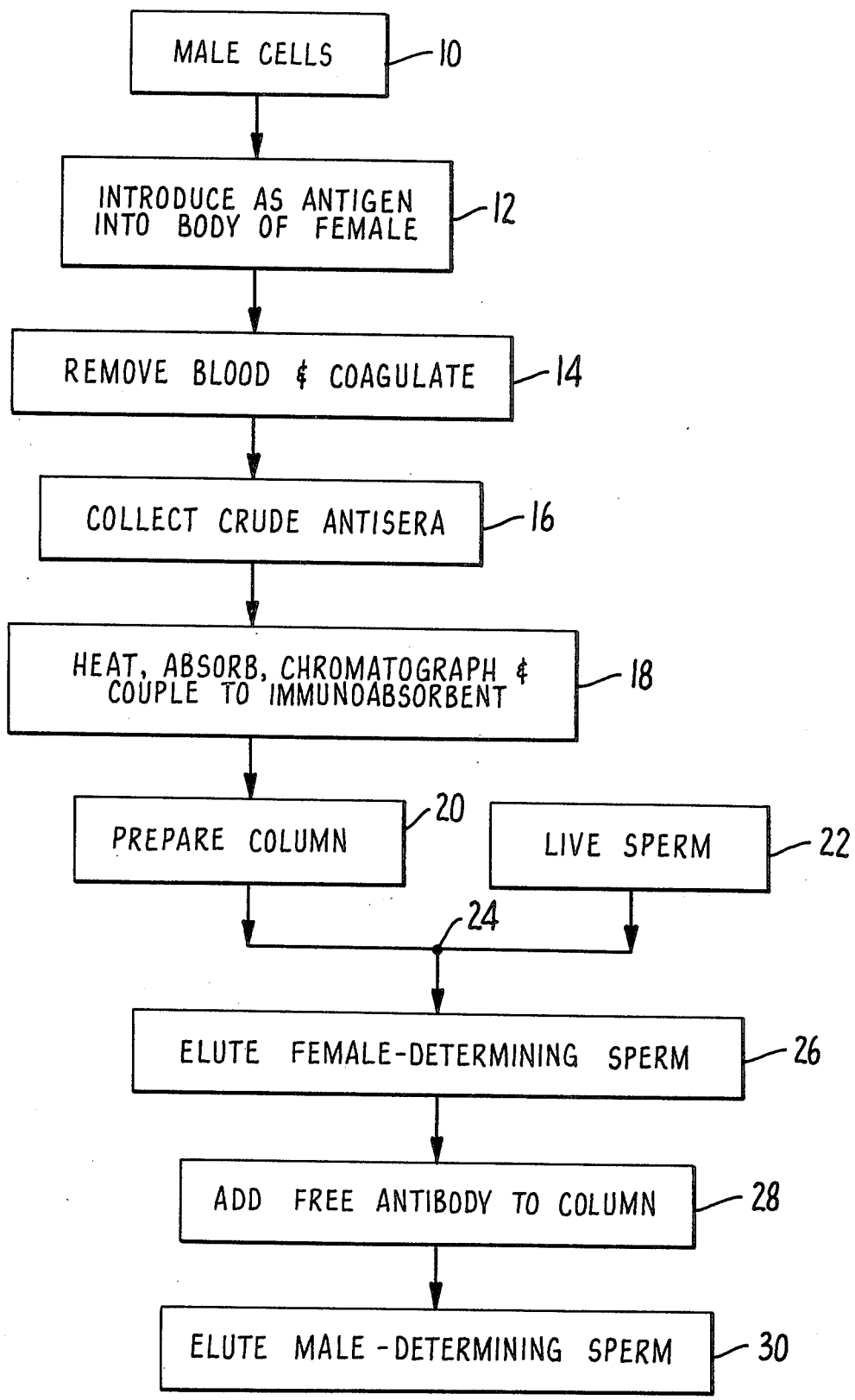

1

METHOD AND MATERIAL FOR INCREASING THE PERCENTAGE OF MAMMALIAN OFFSPRING OF EITHER SEX

BACKGROUND OF THE INVENTION

1. Field of the Invention

My invention relates to methods, apparatus and materials for increasing the percentage of mammalian offspring of either sex, and more particularly to immunological methods of increasing the percentage of mammalian offspring of either sex, apparatus for carrying out such immunological methods, and seminal fluid materials obtained by using such methods, containing either male-determining spermatazoa or female-determining spermatazoa in substantial perponderance as compared with naturally occurring, unmodified semen.

2. Description of the Prior Art

Mechanical methods increasing the percentage of mammalian offspring of either sex by providing seminal fluids containing a surplus of either male-determining spermatazoa of female-determining spermatazoa with the aid of the difference in density between male-determining spermatazoa and female-determining spermatazoa are taught in the prior art, e.g., in abandoned United States Patent application Ser. No. 443,473, in United States Patent application Ser. No. 814,906, and in a paper by E. Schilling, "Separation of Bull Sperm by Sedimentation and Centrifugation and the Sex of the Born Cows," Zeitschrift fur Saugertierkunde, Volume 31, No. 4, pages 314-323 (1966). Such methods are known, however, to be characterized by reduced sperm survivability, and by reduced viability of the surviving sperm.

The speculation that immunological means can be used to increase the percentage of mammalian offspring of either sex is discussed in a paper entitled "Sex Ratio in Progeny of Mice Inseminated With Sperm Treated With H-Y Antiserum" by Bennett and Boyse, Nature, Volume 246, Nov. 30, 1973, pages 308 and 309.

An immunological method of increasing the percentage of mammalian offspring of either sex is disclosed in United States Pat. No. 3,687,806, issued to Gustaaf J. van den Boevenkamp on Aug. 29, 1972. The method of this patent required as a starting material a sperm fraction containing a surplus of either male-determining spermatazoa or female-determining spermatozoa isolated in accordance with the aforementioned abandoned application Ser. No. 443,473, the other abovementioned application Ser. No. 814,906, or the aforementioned Schilling article, or closely related mechanical methods. Thus, the method of the aforementioned U.S. Pat. No. 3,687,806 necessarily suffers to a greater or lesser degree from the disadvantages of said mechanical methods, i.e., reduced sperm survival and reduced viability of the surviving sperm.

Summary of the Invention

Accordingly, it is an object of the present invention to provide an immunological method of increasing the percentage of mammalian offspring of either sex without subjecting the required seminal fluid to mechanical separation techniques depending upon the very small density differential between male-determining spermatazoa and female-determining spermatazoa.

In general, it is an object of the present invention to provide a successful method for preselecting the sex of mammalian offspring.

Another object of the present invention is to provide apparatus for carrying out such a method.

Yet another object of the present invention is to provide materials for use in the artificial insemination of mammalian females containing a very substantial preponderance of either male-determining spermatazoa or female-determining spermatazoa.

With the above objects in view, among other objects which will become apparent hereinafter, the present invention is characterized by the following features and aspects, and other features and aspects disclosed hereinbelow.

In accordance with a particular feature of the present invention, a known solid-phase immunoabsorbent system is applied to the separation of X and Y sperms contained in semen samples.

In accordance with another principal feature of the present invention a Y-antigen-specific antibody (hereinafter sometimes called "male-specific antibody" or "anti-Y antibody") is prepared and coupled to an immunoabsorbent material.

In accordance with another feature of the present invention, a male-specific antibody-coupled solid-phase immunoabsorbent material is used to selectively and solely bind male-determining spermatazoa (hereinafter sometimes called "Y-sperm") contained in a sperm suspension, so that female-determining spermatazoa (sometimes hereinafter called "X-sperm") can be directly recovered.

In accordance with another feature of the present invention, a means is provided for releasing immunoabsorbent-bound Y-sperm so that Y-sperm can be recovered.

In accordance with a particular aspect of the present invention, there is provided an immunoabsorbent-coupled male-specific antibody which binds selectively and solely to the Y-antigen, and to no other antigen, expressed on mammalian sperm surface membranes.

In accordance with another aspect of the present invention, method and apparatus are provided by which a given batch of male-specific antibody-coupled immunoabsorbent material can be tested for efficacy prior to use in mammalian sperm fractionation.

Other objects of my invention will in part be obvious, and will in part appear hereinafter.

My invention, accordingly, comprises the several steps and the relation of one or more of such steps with respect to each of the others, the apparatus embodying features of construction, combinations and arrangements of parts which are adapted to effect such steps, and the material which possesses the characteristics and properties, all as exemplified in the detailed disclosure hereinafter set forth, and the scope of the invention will be indicated in the appended claims.

For a fuller understanding of the nature and objects of the invention reference should be had to the following detailed description, taken in connection with the accompanying drawing.

BRIEF DESCRIPTION OF THE DRAWING

The drawing is a flow sheet illustrating the method of my invention.

DETAILED DESCRIPTION OF THE PREFERRED EMBODIMENTS

As shown in the drawing, the method of my invention comprises preparing a male-specific antibody (sometimes called a "Y antigen-specific antibody" or "anti-Y antibody"): coupling said male-specific antibody to a solid-phase immunoabsorbent material; adding native semen to said male-specific antibody coupled solid-phase immunoabsorbent material and eluting female-determining spermatazoa directly; treating said solid-phase immunoabsorbent material containing bound male-determining sperm to inhibit the binding of the male-determining spermatazoa; and eluting the male-determining spermatazoa from said solid-phase immunoabsorbent material.

Experience with the method of my invention leads to the expectation that by its use seminal fluids (i.e., fluids suitable for use in artificial insemination, containing a substantial preponderance of male-determining spermatazoa or female-determining spermatazoa (Y-sperm or X-sperm)) may be provided which contain ten percent or fewer of undesired spermatazoa, and that these seminal fluids are fertile in artificial insemination and are strongly preselective for the desired sex of the offspring. Said experience also shows that a male-specific antibody prepared in one mammalian species by the method of my invention can be used to separate sex-determining spermatazoa of other mammalian species, i.e., the male-specific antibody is to some extent immunologically cross-reactive between species.

Referring now to the drawing, a generalized example illustrating the practice of the method of my invention, the structure of the apparatus of my invention, and the seminal fluids of my invention, will now be described in detail. It is to be understood, however, that my invention is not limited to the particular methods, apparata, and seminal fluids described in detail hereinbelow, since many variations in the below-described specific methods, apparata, and seminal fluids will occur to those having ordinary skill in the art of immunology, upon being informed by my present disclosure, without the exercise of invention.

As will be evident to those having ordinary skill in the field of immunology from examination of the drawing, the technique of isolating male-specific antibody selected for use in carrying out the abovesaid generalized example of the method of my invention is the technique of animal immunization with Y antigen. As is known to those having ordinary skill in the art, however, male-specific antibody can be isolated from the blood sera in which it occurs by several other techniques well-known in the art of immunology, and thus my method invention is not limited to the employment of animal immunization techniques for the production of the required male-specific antibody.

By way of example, however, and by way of example only, the following animal immunization technique, based upon the fact that Y antigen capable of eliciting male-specific antibody in the blood of female recipients is found on epidermal cells and sperm heads of male rodents, may be used to provide the male-specific antibody required for carrying out the method of my invention.

Female rabbits are hyper-immunized by intraperitoneally injecting 500 million trypsin-dissociated epidermal cells from male rabbits in a series of twice-weekly injections lasting 6 weeks. Six days after the last injection the female rabbits are exsanguinated. The blood samples thus obtained are allowed to clot, and crude antisera are isolated, complement-inactivated by heating at 56° C. for 30 minutes, and then pooled. Undesired antibodies are then removed from the crude antiserum pool by a series of fifteen repeated absorptions using equal volumes of packed, washed female rabbit spleen cells combined from several individuals. The absorbed antiserum pool is finally fractionated by agarose gel filtration according to the method of Hannon (Journal of Immunological Methods, 1975, 8:29). The fraction representing gamma globulin G is isolated and stored at −20° Celsius until used in further carrying out of the method of my invention.

As will be understood by those having ordinary skill in the art of immunology, the just described technique of raising and refining the required male-specific antiserum or anti-Y antiserum is, in accordance with one teaching of my invention, especially well adapted to assure the monospecificity of the antiserum. That is, to assure that the antiserum thereby raised and refined, and intended for application in sperm fractionation, will contain antibody capable of binding to the Y antigen, but to no other antigens, expressed by sperm surface membranes. Antisperm antibodies other than anti-Y or male-specific could diminish both the precision of the sperm fractionation process of my invention and the fertility of the resulting seminal fluid material of my invention.

It is to be particularly noted that the just described technique, in accordance with a particular aspect of my invention, employs epidermal cells, rather than sperm heads or whole sperm, as the immunizing male tissue, although sperm heads or whole sperm have been used for the same purpose in the prior art, even though it is obvious that undesired sperm-specific antibodies may be induced by this tissue, which could be difficult to remove from the crude antisera by subsequent absorption procedures.

The monospecificity of the male-specific antiserum obtained by the just described technique may be tested by coupling a portion of it with fluorescein isothiocyanate. In carrying through this test of the present invention the fluorscent-tagged antiserum is combined with human spermatazoa in a direct fluoresence microscopic preparation. Bright fluorescence of approximately 50 percent of the sperm indicate specific binding of the fluorescent tagged male-specific antiserum by Y sperm. The lack of staining of the remaining approximately 50 percent of the sperm, i.e., the X sperm, indicates the essential monospecificity of the antiserum produced by the just described technique for the Y antigen.

Referring now to the drawing, it will be seen that the just described male-specific antiserum or antibody preparation technique is represented by the rectangles 10, 12, 14, and 16 of the drawing.

As will also be evident to those having ordinary skill in the art reviewing the drawing, the immediately above described antiserum monospecificity test, if shown in the drawing, which it is not, would immediately follow the agarose gel chromatography indicated in the step of reference numeral 18.

Referring again to the drawing, it will be seen that after the collection of the crude antisera as noted in the step of reference numeral 18 and its refinement by heat, repeated absorptions and chromatographic fractionation by agarose gel filtration, all of which steps are denoted by reference numeral 18, and after the above-described monospecificity test, the refined antiserum is coupled to a solid-phase immunoabsorbent material, as noted under reference numeral 18.

It is noted that, in accordance with a particular aspect of the invention, it is preferred to alter the concentration of the bulk portion of the antiserum to one milligram per milliliter in phosphate buffered saline, pH 7.4, prior to immunoabsorbent coupling.

The said immunoabsorbent coupling, i.e., coupling of the previously produced male-specific antibodies to solid-phase immunoabsorbent material may be carried out as follows.

Sephadex G-200 beads (Pharmacia) are seived to provide 60 milliliters of beads to a size of 80 to 120 micrometers. The thus-seived beads are activated with 100 milligrams of cyanogen bromide at pH 10.2 for 10 minutes, resulting in a 20 to 30 percent reduction in volume. This activation treatment renders the immunoabsorbent material capable of accepting protein molecules by covalent bonding. The activated beads are washed in borate-buffered saline at pH 8.3. 20 milligrams (20 milliliters) of monospecific male-specific antibody are added to the washed, activated beads, which first have rested at room temperature for about 4 hours without mechanical stirring. The resulting Sephadex G-200 anti-Y antibody conjugate is washed with phosphate-buffered saline over a sintered glass funnel without suction, mixing every 15 minutes with a glass rod.

The thus washed immunoabsorbent-anti-Y conjugate is used to prepare a series of columns by packing 12 milliliter plastic, disposable syringes, fitted with a polyethylene retainer disk instead of a piston, with eight to ten milliliters of the conjugate.

These columns are washed prior to sperm fractionation with medium 199 containing 50 percent fetal calf serum by volume, 2.5 millimolar ethylenediamine tetraacetic acid by weight and 1 percent penicillin streptomycin by volume (hereinafter called "medium no. 1".)

Having thus prepared the fractionation columns (reference numeral 20 in the drawing), live sperm (reference numeral 22 in the drawing) may not be prepared for fractionation in accordance with the method of my invention by the following technique.

The live sperm are dispersed in medium no. 1 and then centrifuged gently. The non-cellular supernatant is decanted from the centrifugation vessel, and then the sedimented sperm are resuspended in fresh medium no. 1. The sperm suspension in fresh medium no. 1 is centrifuged gently, and the supernatant non-cellular material again decanted from the centrifugation vessel. The sedimented sperm from the second decanting step is then suspended in a new medium, i.e., medium 199 containing 50 percent fetal calf serum by volume and 2.5 millimolar ethylenediamine tetraacetic acid by weight (hereinafter called "medium no. 2"), in a concentration of 10 to 20 million cells per milliliter. This sperm suspension, sometimes hereinafter called the "prepared sperm suspension", is ready for application to the prepared immunoabsorbent columns.

As indicated in the drawing by reference numeral 24, the prepared sperm suspension may now be applied to the previously prepared fractionation columns in accordance with the following technique.

A 5 to 10 milliliter portion of the just described prepared sperm suspension is applied to each 8 milliliter column at room temperature. Eluates comprising the X sperm fraction are collected from the columns by stepwise elution with 15 milliliter amounts of the abovesaid medium no. 2 at a flow rate of approximately 0.3 to 0.5 milliliters per minute, continued until the effluent is virtually cell-free. This elution of the female-determining sperm is indicated by the reference numeral 26 in the drawing.

Having eluted substantially all of the female-determining spermatazoa from the fractionation columns, the male-determining spermatazoa may be recovered from the fractionation columns in accordance with the following technique.

A quantity of medium no. 2 re medium 199, a commercially available tissue culture medium sold by Digco of Detroit, Mich., to which is added fifty percent fetal calf serum by volume and 2.5 millimolar ethylene diamine tetraacetic acid [EDTA] by weight, is supplemented with 10 milligrams of male-specific antibody per milliliter. The antibody-supplemented medium hereinafter is called "medium no. 3".

Eluates comprising the male-determining spermatazoa are collected from the fractionation columns by stepwise elution with 15 milliliter amounts of medium no. 3.

As seen in the drawing, such elution with medium no. 3 subserves the two steps of adding free antibody to the fractionation columns (reference numeral 28) and eluting the male-determining spermatazoa from the fractionation columns (reference numeral 30).

As will be evident to those having ordinary skill in the art of immunology, then, the male-determining sperm fraction is eluted from the fractionation columns, in accordance with the principles of the present invention, by employing the well-known principle of competitive inhibition of cellular binding.

In accordance with a further teaching of the present invention, the contents of the fractionation columns will preferably be gently mixed during the elution of the male-determining sperm fraction by carefully drawing the immunoabsorbent beads up and down in a Pasteur pipet. Further, in accordance with the teachings of the present invention, this gentle mixing action by pipet will preferably be continued until the effluent from the fractionation columns is virtually cell-free.

In accordance with another aspect of the present invention, it is preferred that the male-determining and female-determining sperm eluates both be washed, i.e., centrifuged and then resuspended, three times in medium 199 containing 5 percent fetal calf serum by volume (hereinafter called "medium no. 4") prior to testing for remaining fractional content of undesired sperm.

While the just described technique of freeing immunoabsorbent-bound male-determining sperm from the fractionation columns, employing the principle of competitive inhibition, may be successfully used in carrying out the method of my invention, it is to be understood that the method of my invention is not limited to the employment of this particular competitive inhibition technique, since alternative techniques are well-known to those having ordinary skill in the art of immunology. Such alternative techniques include enzymatic digestion of the immunoabsorbent and alteration of pH or salt concentration of the medium. Other techniques will occur to those having ordinary skill in the art of immunology without the exercise of invention.

Seminal fluids for artificial insemination materials of my invention, prepared by the steps and techniques set out hereinabove, have been tested for (i) the efficacy of separation in sperm suspensions prepared from one species of mammal, and (ii) the fertility of the separated sperm fractions in a second species of mammal.

Efficacy according to (i) was measured by criteria of total cell recovery and degree of X and Y sperm separation attained in the fractions. The quinacrine fluorochrome, a cellular stain known in the prior art to be specific for the presence of the Y chromasome in human sperm, was used in this test. The results of this test showed that Y fractions containing 89 percent or more of Y positive cells and X fractions containing 6 percent or fewer of Y positive cells were obtained with a sperm loss of 18 percent or less (Table I).

Fertility according to (ii) was measured by sex preselection trials in mice. Pooled epidermal and vas deferens sperm from male mice were fractionated and brought to a concentration of five million sperm per 0.1 milliliter in medium no. 4. Recipient females were each inseminated with five million sperm at 24 to 30 hours post partum. Control females were mated to male mice at 24 to 30 hours post partum. The results showed that insemination with male-determining seminal fluids or female-determining seminal fluids prepared in accordance with the method of my invention strongly pre-selected the sex of the offspring, resulting in fewer than ten percent of undesired issue by sex (Table II).

These data are statistically significant at the level of 0.001 by Chi-X Square test. The fact that a 60 percent conception rate was achieved in this test speaks well for the fertility of the seminal fluids or artificial insemination materials produced by the method of my invention, when compared with the well-known technical difficulties in the artificial insemination of mice as shown by the comparable conception rates which were obtained in trials with unfractionated mouse sperm suspension. The offspring sex ratios attained in these tests (Table II) conform closely to the sex ratios expected on the basis of residual contamination of the inseminated fractions by sperm of the undesired sex chromosome type as observed in the fluorescent malespecific antibody staining tests referred to hereinabove. It is believed, then, that the expected sex ratio to be achieved by any particular batch of seminal fluid or artificial insemination material of the present invention can therefore be predicted by such testing.

It is believed to be apparent from the foregoing that an anti-male-rabbit-specific antibody raised in female rabbits, treated in accordance with a method of my invention to produce artificial insemination materials of my invention, can effect a separation of male-determining and female-determining spermatazoa in semen from mice and humans. This result accords with data from the scientific literature which indicate that the Y antigen of mammals exhibits the property of extensive immunological cross-reactivity between species.

It will thus be seen that the objects set forth above, among those made apparent from the preceding description, are efficiently attained, and, since certain changes may be made in carrying out the above methods, and in the apparatus described, and in the artificial insemination material set forth, without departing from the scope of the invention, it is intended that all matter contained in the above description and shown in the accompanying drawing shall be interpreted as illustrative and not in a limiting sense.

It is particularly noted that the method of the present invention, employing as it does a solid-phase immunoabsorbent system which permits mammalian X and Y sperm to be separated by differential binding of Y sperm to the immunoabsorbent, rather than by mechanical methods relying upon the very small differential density between X sperm and Y sperm, is fully reversible so that Y sperm or male-determining sperm can be recovered without the cellular damage attending conventional cellular agglutination, cytolysis, or other means of cellular inactivation. It is believed that the importance of these properties of the method of my invention for fertility and precision in separated sperm fractions intended for sex preselective artificial insemination purposes cannot be overestimated.

The test data from the efficacy test (i) and fertility test (ii) referred to above are as follows:

Table I.

Human X and Y sperms before and after fractionation using immunoabsorbent-anti-Y antibody conjugate.

| Trial | Y positive cells (%)[1] | | Sperm Recovery (%)[2] | |
|---|---|---|---|---|
| | Unfractionated | X fraction | Y fraction | |
| 1 | 47 | 2 | 92 | 82 |
| 2 | 48 | 5 | 93 | 82 |
| 3 | 45 | 4 | 90 | 88 |
| 4 | 48 | 6 | 89 | 89 |

[1] Based on counts of 200 quinacrine stained cells/category
[2] Based on dividing cells in combined fractions by cell input into column.

Table II.

Sex preselective capacity of mouse sperm fractionated by means of anti-Y antibody coated immunoabsorbent.

| Male Births (%)[1] | | |
|---|---|---|
| Control | X Fraction | Y Fraction |
| 46.6 | 4.2 | 92.3 |

[1] based on 150 or more births/category.

From the foregoing, it is believed to be apparent that the completely immunological, and not-mechanical, method of my invention has great utility in controlling the sex of mammalian offspring. It is further believed that the method, apparatus, and artificial insemination materials of my invention are especially important in commercial application in the field of animal husbandry for example, in permitting the breeder or farmer to have a choice in selecting the sex of animal offspring. By way of illustration, the dairy farmer can elect to obtain only female off-spring and thereby breed only milk-producing cows, rather than bulls. Regarding human procreation, my invention provides parents with a simple, easily employed means to select or control the sex of their offspring, in that they may satisfy the desire to have a child of a particular sex, thus limiting family size and contributing to the reduction of world population problems.

It is also to be understood that the following claims are intended to cover all of the generic and specific features of my invention herein described, and all statements of the scope of my invention, which, as a matter of language, might be said to fall therebetween.

Having described my invention, what I claim as new and desire to secure by Letters Patent is:

1. As a new composition, a conjugate of activated solid phase immunoabsorbent material having monospecific malespecific antibodies capable of binding male specific sperm distributed over the surface of said immunoabsorbent material and coupled thereto.

2. The composition of claim 1 in which said activated solid phase immunoabsorbent material is in the form of a plurality of discrete beads.

3. The composition claimed in claim 2 in which said plurality of beads comprise polysaccharide beads disposed in a column.

4. The composition of claim 1 wherein said immunoabsorbent material, has been activated to render it capable of accepting protein molecules by covalent bonding, by the treatment thereof with a cyanogen halide.

5. The composition of claim 3 wherein said polysaccharide beads have been activated to render them capable of accepting protein molecules by covalent bonding by treatment with a cyanogen halide.

6. The composition of claim 5 wherein the cyanogen halide is cyanogen bromide.

7. A process for separating male and female determining sperm from native semen which comprises:
   (a) coupling monospecific male specific antibodies to a solid phase immunoabsorbent substrate to form a conjugate,
   (b) loading a separation column with the monospecific male specific conjugate,
   (c) passing semen containing male and female determining sperm through the column,
   (d) separating out the female determining sperm from the column, and
   (e) separating out the male determining sperm from the column.

8. The process of claim 7 wherein the step of separating out the male determining sperm comprises passing a composition consisting essentially of monospecific male specific antibody through the column.

9. The process of claim 7 wherein the coupling step (a) comprises:

activating the solid phase immunoabsorbent material to render it capable of accepting a protein by covalent bonding, and adding a solution of monospecific male specific antibody thereto.

10. The process as claimed in claim 7 in which said body of semen contains the naturally-occurring ratio of male-determining spermatazoa to female-determining spermatoazoa prior to said separation of male-determining spermatazoa.

11. The process as claimed in claim 8 further comprising:
   incorporating said male-determining spermatazoa into a fluid medium suitable for use in artificial insemination; and
   artificially inseminating a female of the same species with said fluid medium containing said male-determining spermatazoa.

12. The process as claimed in claim 7 further comprising:
   incorporating said female-determining spermatazoa into a fluid medium suitable for use in artifical insemination; and
   artificially inseminating a female of the same species with said fluid medium containing said female-determining spermatazoa.

13. The method of increasing the percentage of mammalian offspring of either sex, comprising the step of selectively separating male-determining spermatazoa by contacting a body of seman with a male specific antibody capable of binding male specific sperm, said antibody being coupled to immunoabsorbent material.

14. The method as claimed in claim 13, further comprising the step of altering the immunoabsorbent material to release male-determining spermatazoa.

* * * * *